US009715577B2

(12) United States Patent
Gross

(10) Patent No.: US 9,715,577 B2
(45) Date of Patent: Jul. 25, 2017

(54) PATIENT IDENTIFICATION DISAMBIGUATION SYSTEMS AND METHODS

(75) Inventor: Brian D. Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 914 days.

(21) Appl. No.: 13/384,346

(22) PCT Filed: Jun. 15, 2010

(86) PCT No.: PCT/IB2010/052690
§ 371 (c)(1),
(2), (4) Date: Jan. 17, 2012

(87) PCT Pub. No.: WO2011/010232
PCT Pub. Date: Jan. 27, 2011

(65) Prior Publication Data
US 2012/0117099 A1    May 10, 2012

(51) Int. Cl.
*G06F 17/30* (2006.01)
*G06F 19/00* (2011.01)

(52) U.S. Cl.
CPC ...... *G06F 19/322* (2013.01); *G06F 17/30303* (2013.01); *G06F 19/327* (2013.01)

(58) Field of Classification Search
CPC ......... G06F 17/30867; G06F 17/30749; G06F 17/30761; G06F 17/30; G06F 19/322; G06F 17/30303
USPC .......................................... 707/749, 752, 754
See application file for complete search history.

(56) References Cited

U.S. PATENT DOCUMENTS

| | | | |
|---|---|---|---|
| 6,523,019 B1* | 2/2003 | Borthwick | 706/45 |
| 2005/0228238 A1* | 10/2005 | Monitzer | 600/300 |
| 2006/0161065 A1* | 7/2006 | Elion | 600/509 |
| 2006/0217623 A1* | 9/2006 | Morganroth | 600/509 |
| 2007/0129636 A1 | 6/2007 | Friedman et al. | |
| 2007/0180047 A1 | 8/2007 | Dong et al. | |
| 2008/0162185 A1* | 7/2008 | Klabunde et al. | 705/2 |

(Continued)

FOREIGN PATENT DOCUMENTS

| | | |
|---|---|---|
| WO | 2006051464 A1 | 5/2006 |
| WO | 2006126107 A1 | 11/2006 |

OTHER PUBLICATIONS

Cruz-Correia, Ricardo João, et al. "Data quality and integration issues in electronic health records." Information discovery on electronic health records(2009): 55-95.*

(Continued)

*Primary Examiner* — Nan Hutton

(57) ABSTRACT

A method for patient ID resolution in recordation of patient data acquired by a medical device (10) comprises: receiving patient data from the medical device comprising pre-gap patient data (50) followed in time by a time gap (52) followed in time by post-gap patient data (54); receiving one or more timestamped patient ID entries (56, 58) associated with the received patient data; associating first patient ID information with the pre-gap patient data; and associating second patient ID information with the post-gap patient data; wherein the associating operations are based on the one or more timestamped patient ID entries (56, 58) associated with the patient data.

11 Claims, 5 Drawing Sheets

(56) References Cited

U.S. PATENT DOCUMENTS

2009/0048865 A1* 2/2009 Breazeale, Jr. .................. 705/2
2009/0116710 A1* 5/2009 Futami et al. ................ 382/128
2009/0119124 A1* 5/2009 Kambaloor ...................... 705/2

OTHER PUBLICATIONS

Sharples, Sarah, et al. "Medical device design in context: A model of user-device interaction and consequences." Displays 33.4 (2012): 221-232.*

* cited by examiner

Figure 2I:
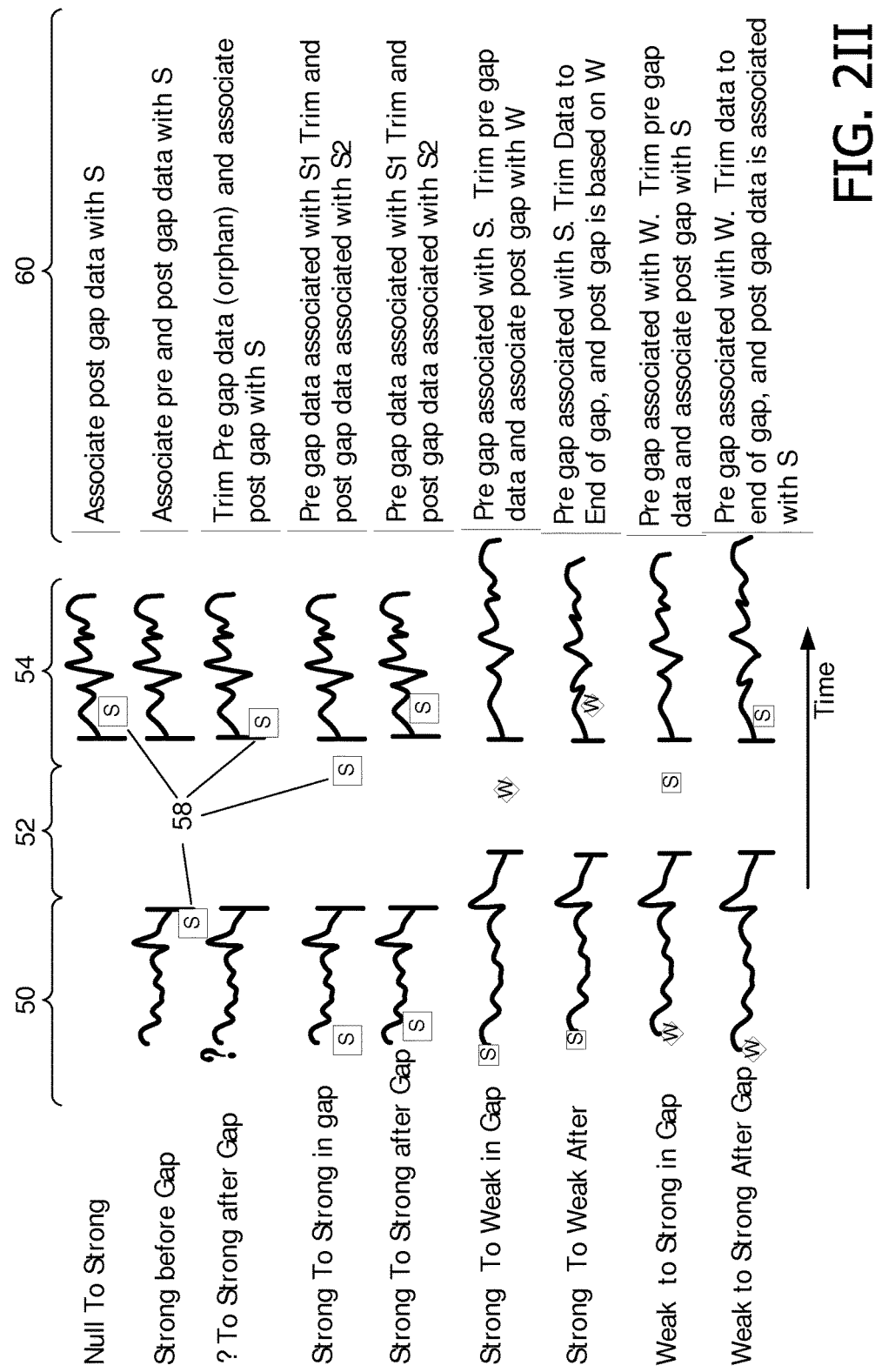

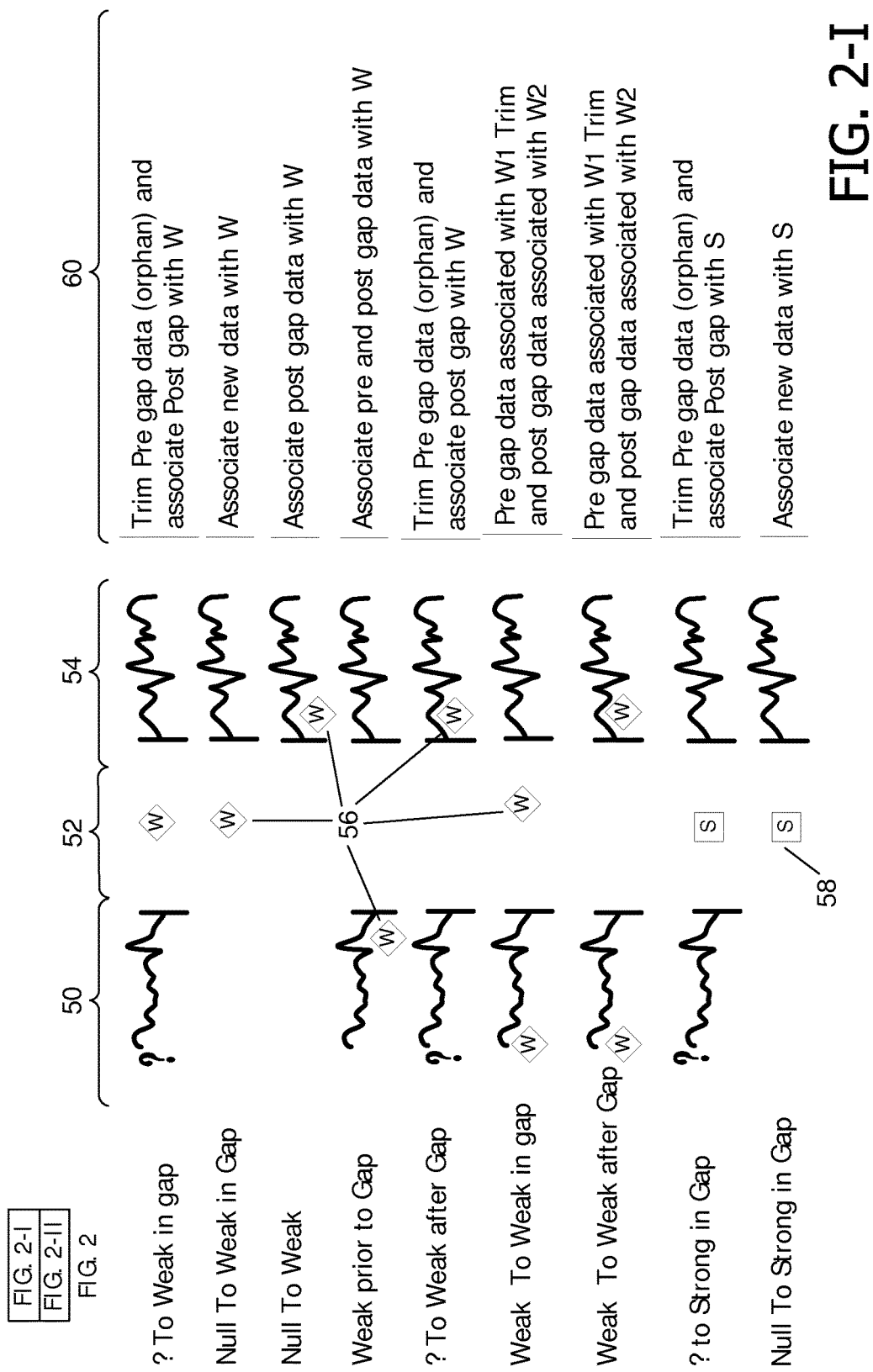
FIG. 2-I

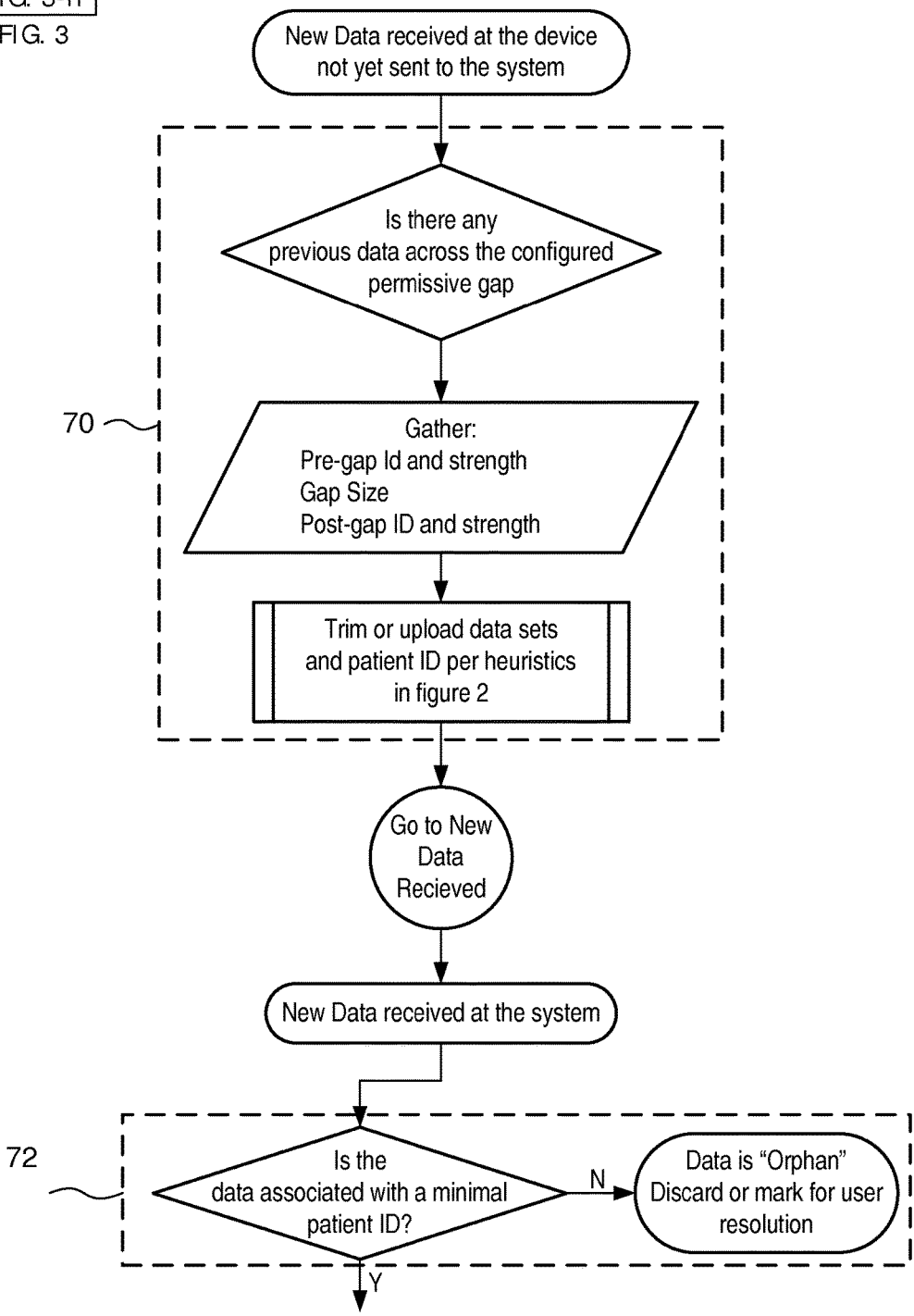
FIG. 3-I

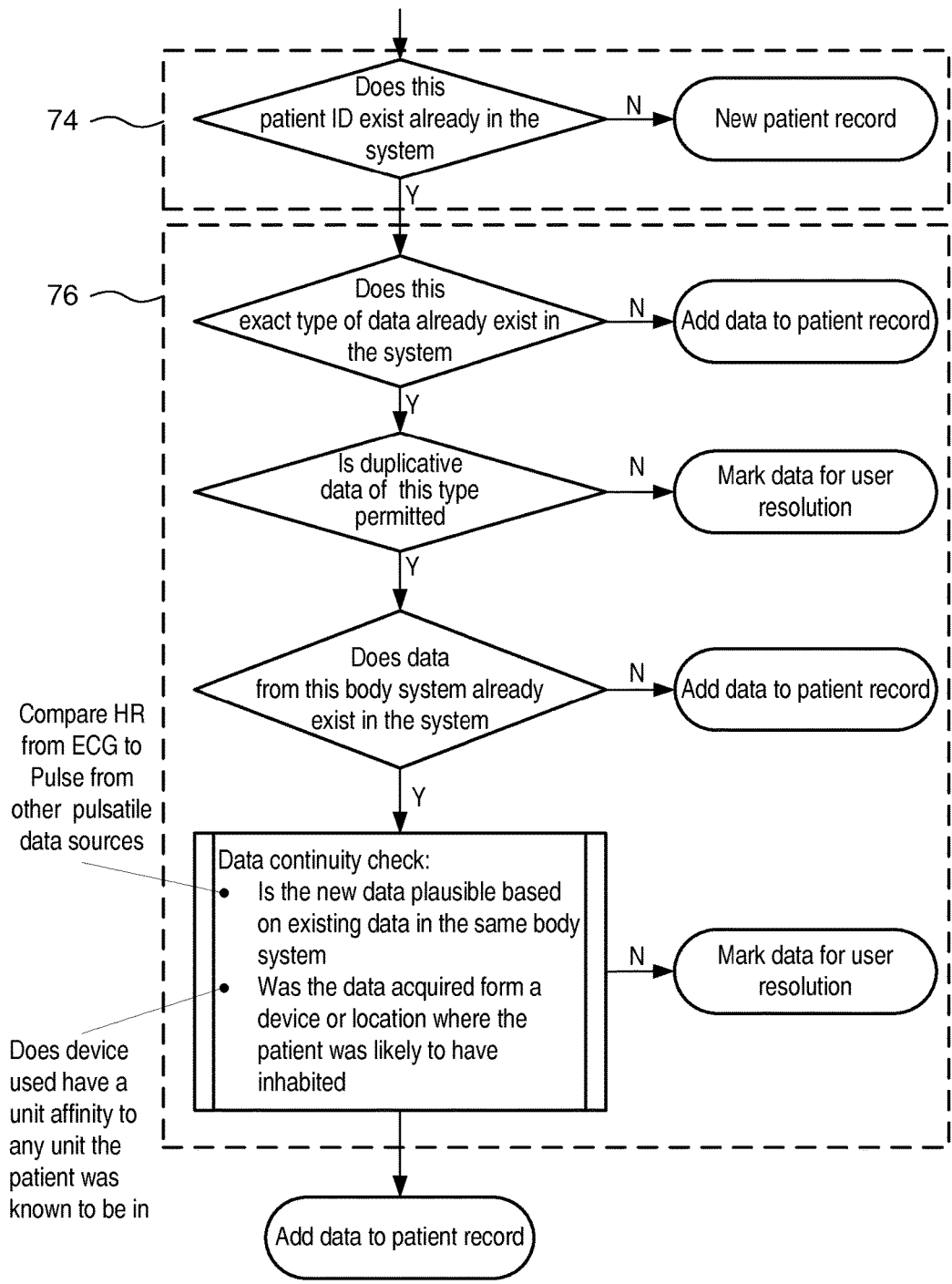
FIG. 3-II

PATIENT IDENTIFICATION DISAMBIGUATION SYSTEMS AND METHODS

CROSS REFERENCE TO RELATED APPLICATIONS

This application claims the benefit of U.S. provisional application Ser. No. 61/227,268 filed Jul. 21, 2009, which is incorporated herein by reference.

The following relates to the medical arts, medical monitoring arts, physiological monitoring arts, patient safety arts, and related arts.

In medical settings, a plethora of patient monitoring and therapy devices are utilized. Some examples include electrocardiograph (ECG) monitors, pulse oxymeter monitors or other vital sign or health wellness indicator data generators, infusion pumps for providing intravenous therapy, temporary cardiac pacemaker controllers, point of care blood analysis, and so forth. These devices may be mobile to the extent that they can be wheeled or otherwise transported from patient room to patient room. Alternatively, if the device is not readily transportable, the patient may be brought to the device. In either case, the device is assigned to a patient, then cleaned, and reassigned to the next patient as appropriate. Such devices generate patient data such as ECG or plethysmograph traces (typically measured as digital samples at a selected sampling rate), intravenous feed data (for example, feed rate in milliliters per minute, again sampled at a selected sampling rate), user entered qualitative or quantitative assessments of health, or so forth.

A nurse, clinician, or other ancillary medical person associates a patient identification (ID) to the device in order for the acquired patient data to become part of the electronic chart or record. This can be accomplished in various ways, such as manual input of the patient ID using a keyboard or other data entry device, reading a barcode on a patient bracelet using a barcode scanner, wirelessly reading a radio frequency identification (RFID) or infrared identification (IRID) tag on the patient bracelet, employing a local area network (LAN) coupled device (CCL), receiving an external patient administration (ADT) message from an external system, or so forth. For some devices, multiple patient ID association methods may be available—for example, a barcode scanner may be used if the patient has been admitted to the hospital, but if the patient is an outpatient lacking a patient bracelet with the appropriate barcode then a nurse may enter the patient ID information manually. In the case of an unconscious or incoherent patient, there is also the possibility that patient ID information may be incomplete.

In any event, the acquired patient data are associated with the patient ID (whether received manually, by barcode scanner, RFID, or so forth) and the acquired patient data associated with the patient ID are communicated from the device to a hospital records system where data are stored and may be retrieved for analysis, display, or so forth. Depending on the communication pathway data transfer may occur continuously, or at discrete intervals such as whenever the device is plugged into a communication port or whenever the device comes within range of a wireless communication link or whenever a data collection algorithm is executed by the hospital records system. For intermittent communication pathways, data are stored in the device until the communication pathway becomes available.

A requisite for this system to work properly is accurate association of patient data with the correct patient—however, frequent transfer of the device from one patient to another presents substantial opportunities for patient ID errors. As more and more discrete data collection devices are used for patient care the patient ID may become ambiguous or conflicted based on the last admit state of a device used, the current system patient ID state, and the connection history of the device to the system. Other sources of patient ID ambiguity include human error—for example, the clinician forgets to remove the patient ID, enters an incorrect patient ID, or never enters a patient ID during a patient monitoring or therapy session.

As devices which are capable of sourcing continuous data (like ECG waveforms) are used between patients, the waveform data stops for a period of time as the device is cleaned and moved to the next patient (or the next patient is moved to the device). In this time there is a gap of data between the two patients. This gap may normally occur for the same patient if, for example the ECG leads become disconnected from the patient or the battery operated device exhausts it finite power source. Some devices will automatically loose the patient ID in this gap period by design, or prompt the user for confirmation of the patient ID. The size of the permissive gap is variable based on the use model for the device. For example, if the device is used for multipatient spot checks, the gap should only be long enough for the user to clean the device and move it to the next patient; otherwise there is a risk that the 2 different patient's data across the gap will be misinterpreted by the system as one patient. This creates an opportunity for the data to become anonymous or incorrectly marked with patient ID based on user error. In such cases, the patient ID association of the patient data is ambiguous. In such cases, it is generally considered best to delete or ignore the patient data, rather than risk associating the data with the wrong patient. However, the consequent loss of patient data can also have adverse consequences, such as loss of diagnostically useful (or even diagnostically crucial) patient data.

Reliance upon human analysts to redress patient ID ambiguity is problematic, due to the possibility of introducing human error. Moreover, in the case of patient ID ambiguity caused by human error, the clinician who committed the error may be the one situated to manually redress the patient ambiguity. In such a case the clinician may be biased toward making a "best guess" as to the patient ID association.

The following provides new and improved apparatuses and methods which overcome the above-referenced problems and others.

In accordance with one disclosed aspect, a patient identification (ID) resolution module comprises a digital processor configured to disambiguate patient ID for patient data having a time gap and including pre-gap patient data preceding the time gap and post-gap patient data succeeding the time gap. The patient ID resolution module (i) associates first patient ID information with the pre-gap patient data and (ii) associates second patient ID information with the post-gap patient data, the associating (i), (ii) being based on one or more timestamped patient ID entries associated with the patient data.

In accordance with another disclosed aspect, a method comprises: receiving patient data comprising pre-gap patient data followed in time by a time gap followed in time by post-gap patient data; receiving one or more timestamped patient ID entries associated with the received patient data; associating first patient ID information with the pre-gap patient data; and associating second patient ID information with the post-gap patient data; wherein the associating operations are based on the one or more timestamped patient ID entries associated with the patient data and wherein the associating operations are performed by a digital processor.

In accordance with another disclosed aspect, a method is disclosed of quantifying the strength of the user ID based on business rules as to aspects such as one or more of the following: minimum amount of data needed to identify the patient (last name encounter number, lifetime number . . . ); a chronology of when the patient ID data was set; the method by which the ID was set (user manually entered, scanned via electronically readable media like barcode or RFID, or from an authoritative system source message); and where the patient and device gathering the data was physically located at the time the data was created.

One advantage resides in reducing patient data loss attributable to patient ID ambiguity.

Another advantage resides in reducing likelihood of erroneous "correction" of patient ID ambiguity.

Another advantage resides in timely prompting of the device operator at the time of data collection, in the case where the data and patient ID is ambiguous and cannot be automatically resolved by the system.

Another advantage resides in reducing likelihood of medical errors attributable to patient ID ambiguity.

Further advantages will be apparent to those of ordinary skill in the art upon reading and understand the following detailed description.

Figure 1:
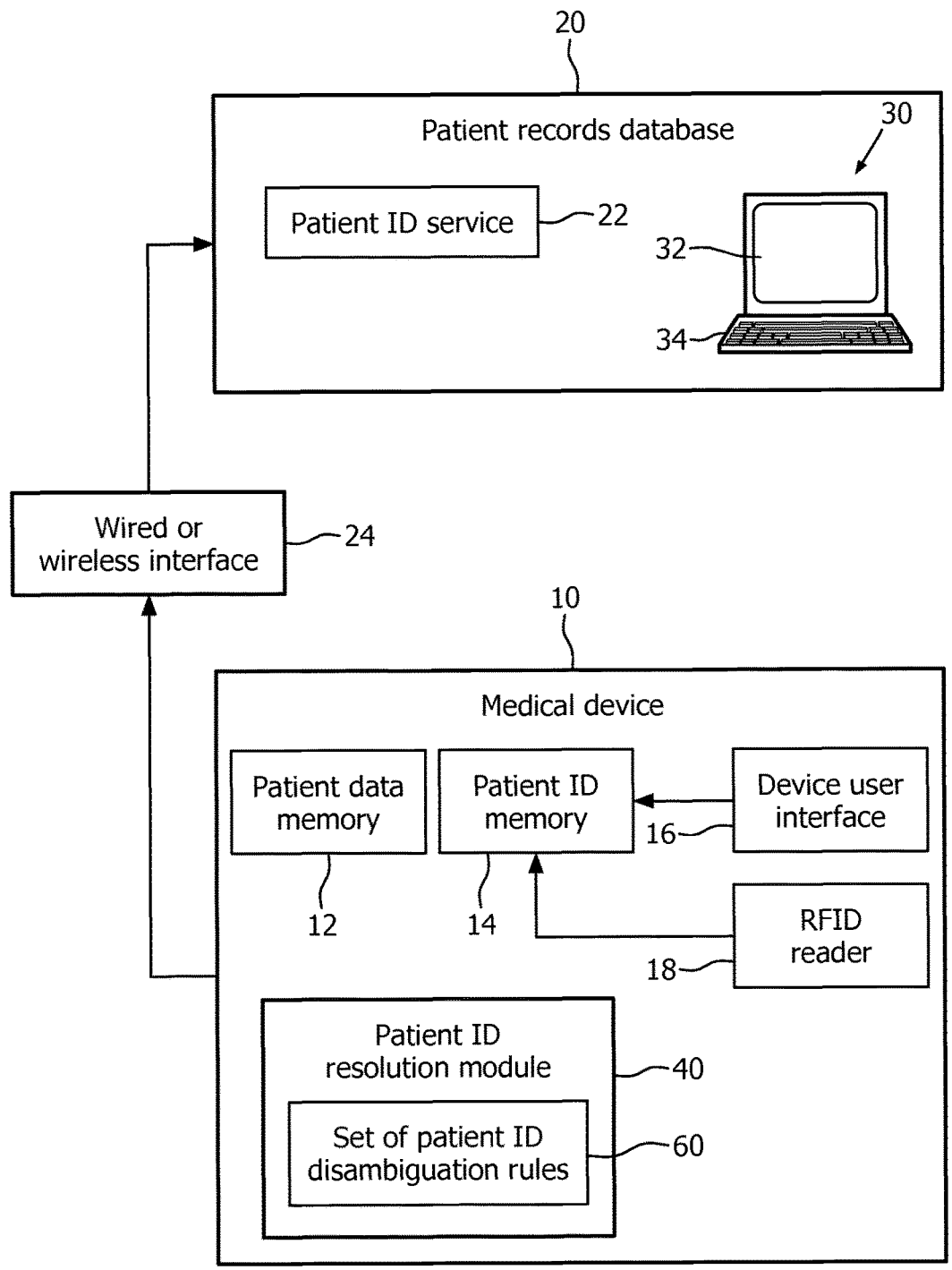

FIG. 1 diagrammatically shows a medical device, patient records database, and communication pathway therebetween.

FIG. 2 diagrammatically shows some illustrative patient ID ambiguity resolution rules suitably performed by the patient ID resolution module of FIG. 1.

FIG. 3 diagrammatically shows a flowchart of an illustrative patient ID ambiguity resolution process suitably performed by the patient ID resolution module of FIG. 1.

With reference to FIG. 1, a medical device 10 performs medical monitoring, patient therapy, or a combination of patient monitoring and therapy. For example, the medical device 10 may be a point of care blood laboratory or biomarker test, an electrocardiograph (ECG) collecting ECG data, a fingertip pulse oxymeter collecting plethysmographic data, a blood pressure monitor collecting blood pressure data, a device to spot check vital signs, qualitative and quantative assessments collected in these devices, or so forth. As other examples, the medical device 10 may be an infusion pump providing intravenous therapy for which the acquired patient data may include intravenous fluid delivery rate as a function of time, or a temporary cardiac pacemaker controller for which the acquired patient data may be delivered stimulation pulse rate as a function of time. The medical device 10 may also include both therapy and monitoring functions—for example, the cardiac pacemaker controller may monitor ECG signals and deliver stimulation pulses only when the ECG signal is abnormal.

The medical device 10 includes a patient data memory 12 that stores acquired patient data, and a patient ID memory 14 that stores patient ID information associated with the patient data. Although illustrated separately, the two memories 12, 14 may be a singular unit, such as a singular FLASH memory, magnetic disk memory, or the like. More generally, the memories 12, 14 may include for example one or more of the following: a magnetic disk or other magnetic data storage medium; an optical disk or other optical data storage medium; a FLASH memory or other electrostatic data storage medium; or so forth. The illustrated memory 12, 14 or another memory may optionally also store firmware or software for controlling operation of the medical device 10.

The stored patient ID information includes an entry timestamp indicating when the patient ID information was entered, the source device, the source device location (if system connected) and an indication of how the ID was entered into the device. The stored patient ID information may include other information such as for example one or more of the following: patient name; patient identification number; patient address; other patient information such as address, age, gender, or so forth; patient-specific medical device configuration information indicating a configuration of the medical device 10 for the patient, device location, data type (vital sign, blood analysis, etc.); or so forth.

In order to receive the patient ID information, the medical device 10 includes two illustrative patient ID entry modalities: (i) a device user interface 16 by which a nurse, clinician, or other user may manually input the patient ID information; and a RFID reader 18 which may wirelessly read an RFID or IRID attached to the patient (for example, disposed in a patient wristband) and including the patient ID information. The device user interface 16 may, for example, include one or more of the following: a keyboard; a touch screen; a voice recognition interface; a trackball, mouse, or other pointing device, bar code scanner, patient area network (PAN) device, capacitive coupled body network (CCBN); or so forth. Optionally, the device user interface 16 may receive other input besides patient ID information. For example, the device user interface 16 may be used to configure the device 10 for a particular patient, or to initiate data transfer, or to initiate a firmware update, or so forth. Moreover, the illustrative patient ID entry modalities 16, 18 are examples, and fewer, more, and/or different patient ID entry modalities may be provided such as a barcode reader, patient administration (ADT) message interface, or so forth.

With continuing reference to FIG. 1, a patient records database 20 provides for collection, storage, and optional data processing of electronic patient records. Toward these ends, an authoritative patient ID service (e.g., a hospital ADT system) 22 interfaces with medical devices such as the illustrative medical device 10 via a wired or wireless interface 24, receives medical data from the medical device 10 via the interface 24, and compares the patient ID information associated with the received device data with how the patient ID is represented in the patient records database 20. The wired or wireless interface 24 may, for example, include one or more of the following: a wireless local area network (WLAN), a Bluetooth interface, PAN, CCBN or other wireless RF link; a wireless infrared link; a universal serial bus (USB), wired Ethernet, or other wired link; or so forth. The wired or wireless interface 24 is illustrated diagrammatically in FIG. 1, and is typically embodied by one or more components disposed in or with the medical device 10 and one or more components disposed with the patient records database 20 (such as for example, a wireless interface card or more generally wireless communication circuitry, an Ethernet card or other network interface card including or operatively connected with a physical Ethernet port, or so forth) and optionally one or more additional intervening communication components such as a wireless router, wireless repeater, an Ethernet hub, IR network, or so forth.

The patient records database 20 and patient ID service 22 are suitably embodied by a network server or other computer or digital data processing and/or storage device, suitably programmed to perform operations providing for patient medical data collection and storage or archiving. Although diagrammatically illustrated as a single unit, these components 20, 22 may optionally be embodied by a plurality of computers or other digital data processing and/or storage devices, such as a plurality of computers networked together, and/or may include a dedicated data storage unit such as a redundant array of inexpensive disks (RAID), or so forth. The patient ID service 22 may optionally receive data from an enterprise master patient record (EMR) source or other authoritative source. In this configuration, the patient ID service 22 implements or is made aware of the business rules in effect to match patient data to the authoritative source such as which data items must be uniquely matched to a known patient, for the data to be considered matched.

The patient records database 20 may optionally be configured to provide data retrieval and display functionality. For example, the illustrative patient records database 20 includes or interfaces with a personal computer 30 including a display 32 and illustrated keyboard 34, mouse, trackball, or other user interfacing device. A nurse, clinician, doctor, or other user can view selected patient data graphically (for example, as an ECG chart), numerically (for example, in tabular form), or in another format via the display 32. The patient records database 20 preferably includes security protocols to limit access to stored patient data based on passwords, fingerprint readers or biometric security devices (not illustrated), or so forth. The information retrieval functionality may optionally include searching based on patient name or other patient identification information, or based on data type or other search criteria. The patient records database 20 may optionally be configured to provide data processing functionality, such as for example processing ECG data to extract a heart rate, processing plethysmographic data to extract heart rate and/or $SpO_2$ information, or so forth.

Patient data transferred from the medical device 10 to the patient records database 20 is generally associated with a patient ID. As already noted, when a user inputs a patient ID the stored patient ID includes an entry date timestamp. In general, newly acquired patient data are associated with last-entered patient ID. However, when time gaps occur in the patient data, the correct association of patient ID with pre-gap patient data preceding the time gap and post-gap patient data succeeding the time gap can be ambiguous.

To resolve patient ID ambiguities at time gaps, a patient ID resolution module 40 is provided, which may be suitably embodied by a suitably programmed digital processor of the sourcing medical device 10 (as illustrated) or by a network server or other computer or digital data processing device with digital processor that embodies the patient ID service 22. To implement the patient ID resolution module 40, the digital processor is configured by software, firmware or the like to execute operations performing patient ID disambiguation.

The patient ID resolution module 40 is illustrated in FIG. 1 as being a component of the medical device 10, for example embodied as a digital processor of the medical device 10 executing operations for performing patient ID disambiguation. In such embodiments the entire system may be completely contained in the device 10. In other contemplated embodiments, the patient ID resolution module may be embodied as a separate stand-alone digital processor, or as part of the patient ID service 22, or as a combination of these data processing devices.

It is to be further appreciated that the patient ID resolution module 40 and optionally other computational components may be embodied by a storage medium storing instructions executable by a digital processor to perform the methods disclosed herein as being performed by the patient ID resolution module 40 and optional other computational components. By way of example, the storage medium may comprise one or more of the following: a hard disk or other magnetic storage medium; an optical disk or other optical storage medium; a flash memory, random access memory (RAM), read-only memory (ROM) or other electrostatic storage medium; or so forth.

With continuing reference to FIG. 1 and with further reference to FIG. 2, the patient ID resolution module 40 resolves patient ID ambiguities across time gaps in the patient data. FIG. 2 diagrammatically shows various situations, where in each case the patient data comprises pre-gap patient data 50 followed in time by a time gap 52 followed in time by post-gap patient data 54. FIG. 2 also diagrammatically denotes timestamped patient ID entries 56, 58, with the timestamps being diagrammatically indicated by the horizontal (time) position of the timestamped patient ID entries 56, 58 relative to the time gap 52.

The timestamped patient ID entries 56, 58 are given strength measures. Timestamped patient ID entries 56 have weak strength measures (for example, because they are manually entered by the user or are not complete or so forth), as diagrammatically indicated in FIG. 2 by representing the timestamped patient ID entries 56 having weak strength measures by diamond symbols labeled "W". Timestamped patient ID entries 58 have strong strength measures (for example, because they are scanned by barcode or are entered by a highly reliable pathway such as RFID), as diagrammatically indicated in FIG. 2 by representing the timestamped patient ID entries 58 having strong strength measures by square symbols labeled "S". The strength measure of a timestamped patient ID entry is a measure of the likelihood that it was a correct patient ID entry. For example, the strength measure may be based on the patient ID entry modality used to generate the timestamped patient ID entry. By way of example, the illustrative medical device 10 of FIG. 1 includes two patient ID entry modalities: the user interface 16 and the RFID reader 18. The user interface 16 is considered a less reliable patient ID entry modality since it is prone to human error—accordingly, timestamped patient ID entries generated by the user interface 16 are assigned a "weak" strength measure. By comparison, the RFID reader 18 is considered a more reliable patient ID entry modality, and so timestamped patient ID entries generated by the RFID reader 18 are assigned a "strong" strength measure.

FIG. 2 also includes a "?" symbol in some rules. This symbol denotes a partial patient ID (for example, a patient ID missing the patient name or identification number so as to be unable to ascertain the patient identity), parameter conflict data, or some other indicator that patient data at the point in time of the "?" indicator may have an unreliable or missing patient ID association.

It should also be noted that for situations depicted in FIG. 2 in which two timestamped patient ID entries occur in succession, it is to be understood that the two timestamped patient ID entries identify different patients. The alternative situation is readily possible, i.e. two successive timestamped patient ID entries may identify the same patient—however, in that case there is no ambiguity regarding the patient ID, and so they are not represented in FIG. 2. For example, the RFID reader 18 may be programmed to acquire a timestamped patient ID entry every few minutes during continuous patient monitoring, with the expectation that those timestamped patient ID entries will continue to indicate the same patient during continuous monitoring.

It is recognized herein that the time gaps 52 are key to resolving patient ID ambiguity. The time gaps 52 represents time intervals during which patient data was not collected. During a time gap it is possible that the medical device was shifted to a different patient. If this is the case, then it follows that the pre-gap patient data 50 should be assigned a different patient ID than the post-gap patient data 54. One expects in this case that a timestamped patient ID entry should be present in the time gap which indicates the medical device being associated with the new (or next) patient.

On the other hand, it is also possible that the medical device was not shifted to a new patient during the time gap 52. In this case, one expects that no timestamped patient ID entry should be present in the time gap.

In some embodiments a time gap of sufficiently short duration (called a "permissive gap") is ignored as it is assumed to be too short to represent a change of patient. The maximum duration of such a permissive gap is optionally a workflow configuration parameter. In care areas where rapid patient throughput is expected devices such as post-anasthesia care units (PACUs) will be configured to have short maximum permissive gaps. On the other hand, medical facilities in which the patient may be "off monitoring" for more extended periods of time may have the maximum permissive gap configured to be of longer duration. In embodiments which include such permissive gaps, the ambiguous patient ID resolution techniques disclosed herein are applied for time gaps which are longer than the maximum duration of a permissive gap.

Ambiguities in the patient ID can arise from various sources. One source of ambiguity is the case in which a timestamped patient ID entry is made during continuous acquisition of patient data, which differs from the patient ID association of immediately previously acquired data. This is an unexpected event since one does not expect patient identification to change during continuous patient data collection, and suggests that at least some data may have ambiguous patient ID association.

Another way an ambiguity can arise is due to a missing or partial patient ID, parameter conflict data, or some other indicator that patient data becomes unreliable—these are the points in time marked by the "?" indicators in FIG. 2.

The patient ID resolution module 40 resolves the patient ID for various data portions based at least on the presence of the time gap 52 across the patient data and timestamps of the timestamped patient ID entries 56, 58 relative to the time gap 52. Other available information may also be utilized in resolving the patient ID ambiguity, such as: information about the physical location of the patient respective to the medical device; the strength measure of the timestamped patient ID entry 56, 58; the medical device type (considering attributes such as portability and whether the device is a pooled device that is shifted from patient to patient on a frequent basis); the device state prior to the timestamp of the timestamped patient ID entry 56, 58 (for example, whether the device was orphaned, free, admitted, or anonymous); and the previous data history (for example, an active stream with a known location for data entering the system, versus present only in the device, as well as data validity). Based on such information, the patient ID resolution module 40 associates first patient ID information with the pre-gap patient data and second patient ID information with the post-gap patient data. Based on these associations, data may be trimmed in the device (end one patient's record and start another), and data fragments of downloaded data have not yet been associated with the patient data record identified and allocated to the appropriate patient.

Patient data acquired by the medical device 10 are analyzed by the patient ID resolution module 40 to ensure correct patient ID association. As a suitable first validation operation, the resolution module 40 optionally checks to see if the parameter represented by the newly received patient data has already been recorded in the patient records database 20 over the same time interval for the patient identified by the associated patient ID using another medical device. If so the patient ID resolution module 40 evaluates whether it is allowable to have duplicative patient data for that parameter. This can be determined based on a suitable business rule operative on the parameter type. For example, heart rate data may come from multiples sources for the same patient (for example, a pulse rate can be obtained from ECG and from a pulse oxymeter) and hence duplicative heart rate data may be deemed allowable; whereas, arterial blood pressure (ABP) data are typically acquired by a dedicated ABP monitor, and so duplicative ABP data are not allowable. If the newly acquired data is duplicative of already-recorded data for the patient, and such duplication is not allowable, then the patient ID resolution module 40 suitably outputs an error, warning, or other indication of the unallowable conflict between the newly received patient data and the duplicative data already stored in the patient records database 20. On the other hand, if the data duplication is allowable, the resolution module 40 optionally performs the further check of comparing the newly acquired patient data with the duplicative patient data already stored in the patient records database 20. If the nominally duplicative data are too dissimilar (for example, as measured by a fuzzy logic comparator, comparison of parameter feature arrays, or the like), the patient ID resolution module 40 suitably outputs an error, warning, or other indication of the unexpected dissimilarity between the newly received patient data and the nominally duplicative data already stored in the patient records database 20.

If the parameter recorded by the newly received patient data is unique to the patient (or is duplicative but passes the optional duplication allowability and similarity validation tests), then the patient ID resolution module 40 optionally checks to see if the location of the acquiring medical device 10 at the time of acquisition of the newly received patient data was reasonably near to the location of the patient at the time of data acquisition, as measured based on location tracking devices associated with the medical device 10 and the patient, respectively. The location tracking devices may be dedicated location tracking devices (for example, GPS locators or triangulators), or may provide locational information as a by-product of other operation (for example, a wireless access point (WAP) that communicates with the medical device 10 provides locational information about the medical device 10 at the time of the wired or wireless communication). Note that this validation test is only available if both the medical device 10 and the patient have location tracking devices both of which were operative at the time the patient data were collected.

Assuming these validation tests are passed, patient ID ambiguity can still arise where some of the patient data was not associated with an unambiguous patient ID or was collected across two patient ID entries in certain conjunctions with time gaps 52 in the patient data collection. Accordingly, the patient ID resolution module 40 is further configured to resolve patient ID ambiguities based on the characteristics of the patient ID association before and after the time gap 52.

With continuing reference to FIGS. 1 and 2, a set of patient ID disambiguation rules 60 operate on timestamps of the one or more timestamped patient ID entries 56, 58 and the time gap 52, as illustrated in FIG. 2. The illustrative patient ID disambiguation rules 60 of FIG. 2 operate based on the temporal position of the timestamped patient ID entries 56, 58 relative to the time gap 52.

Some patient ID disambiguation rules optionally also operate based on the "weak" or "strong" strength measure of the timestamped patient ID entries 56, 58. For example, in FIG. 2 consider the case where a timestamped patient ID entry 56 is generated during acquisition of the pre-gap patient data 50 and no other timestamped patient ID entry is generated (the "Weak prior to Gap" and "Strong before Gap" rules of FIG. 2). In these examples, the rules 60 set forth in FIG. 2 associate both the pre-gap patient data 50 and the post-gap patient data 54 with the patient ID identified by the timestamped patient ID entry 56, 58. However, in other embodiments, it is contemplated to employ different rules based on whether the timestamped patient ID entry is a weak timestamped patient ID entry 56 (as in the "Weak prior to Gap" example) as compared with the case in which it is a strong timestamped patient ID entry 58 (as in the "Strong before Gap" example). The location of the weak timestamped patient ID entry 56 during the acquisition of the pre-gap patient data 50 raises some concern since it implies a nurse or other user manually generated the weak timestamped patient ID entry 56 via the user interface 16 during data acquisition, which is contrary to usual procedure. On the other hand, it is reasonable to expect that the RFID reader 18 may occasionally read the patient RFID tag and generate the strong timestamped patient ID entry 58. Thus, in some embodiments it is contemplated to have the rule for the "Weak prior to Gap" example discard both the pre-gap patient data 50 and the post-gap patient data 54.

With reference to FIG. 3, a flowchart of some optional data validation tests is illustrated. Process operations 70 illustrate patient data collection and patient ID tagging operations. Process operations 72 discard patient data that has incomplete or nonexistent patient ID association, or flags the data for user action to assign the correct patient ID. Process operations 74 generate a new patient record if the patient ID associated with the received patient data does not already exist in the patient records database 20. Process operations 76 perform data validity tests including determining whether the data is duplicative and, if so, whether storage of duplicate data of this type is allowed, and if so whether the duplicative satisfies selected data continuity checks respective to the already-stored duplicate data (e.g., is the new data plausible when compared with the already-stored data in the same body system, and was the new data acquired from a device or location where the patient was likely to have inhabited). Process operations 76 also optionally perform a patient/medical device locational proximity test. In a suitable embodiment, the proximity test checks whether the medical device 10 was located proximate to the patient at the time of the data collection. The proximity test utilizes knowledge of patient location at the requisite time based on history from the patient records database 20 (for example, a recorded hospital room/bed assignment) and concurrent locational information for the medical device 10 (for example, information that the device 10 was connected with a particular WAP or physical port at the time of data collection) to determine whether the patient was proximate to the device 10 when the data were acquired. The validation operations 76 are optionally performed in addition to the rules-based patient ID resolution operations described with reference to FIG. 2.

In the case of a device that can acquire and store multiple patient records, all process operations 70, 72, 74, 76 shown in FIG. 3 can be completed in the medical device 10 by the illustrated patient ID resolution module 40. In other embodiments, the patient ID resolution module 40 includes a component embedded with or in communication with the patient ID service 22 in order to perform operations that utilize information that may be unavailable at the device 10, such as patient locational information that may be available only in the patient records database 20. (In some embodiments, however, such information may be supplied to the patient ID resolution module 40 in the medical device 10 via the wired or wireless interface 24). As previously noted, it is also contemplated for the patient ID resolution module 40 to be wholly embodied by the patient ID service 22.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. An apparatus comprising:
a medical device configured to acquire patient data as a function of time and to receive patient ID entries associated with acquired patient data, the medical device including data memory that stores acquired patient data and timestamped patient ID entries associated with acquired patient data; and
a patient identification (ID) resolution module comprising a digital processor configured to disambiguate patient ID for patient data acquired over a time interval by the medical device, the patient data having a time gap during which the medical device did not acquire patient data and including pre-gap patient data preceding the time gap and post-gap patient data succeeding the time gap and further having one or more timestamped patient ID entries associated with the patient data, the patient ID resolution module (i) associating first patient ID information with the pre-gap patient data and (ii) associating second patient ID information with the post-gap patient data, the associating (i), (ii) being based on the one or more timestamped patient ID entries associated with the patient data and employing a set of patient ID disambiguation rules operating on the timestamps of the one or more timestamped patient ID entries relative to the time gap.

2. The apparatus as set forth in claim 1, wherein:
the first patient ID information is selected from a group consisting of no patient ID and a first patient ID, and
the second patient ID information is selected from a group consisting of no patient ID, the first patient ID, and a second patient ID,
the first and second patient ID being determined from the one or more timestamped patient ID entries.

3. The apparatus as set forth in claim 1, further comprising:
a patient records database configured to store the pre-gap patient data associated with the first patient ID information and the post-gap patient data associated with the second patient ID information, wherein:

the first patient ID information is selected from a group consisting of no patient ID and a first patient ID, and the second patient ID information is selected from a group consisting of no patient ID, the first patient ID, and a second patient ID, the first and second patient ID being determined from the one or more timestamped patient ID entries, the patient records database discarding or marking for later user resolution any patient data associated with no patient ID.

4. The apparatus as set forth in claim 1, wherein the medical device comprises:

one or more patient ID entry modalities, the timestamped patient ID entries associated with the patient data being generated by the one or more patient ID entry modalities.

5. The apparatus as set forth in claim 4, wherein:

the one or more patient ID entry modalities include at least a first patient ID entry modality and a second patient ID entry modality, the timestamped patient ID entries associated with the patient data have strength measures based on the patient ID entry modality used to generate the timestamped patient ID entries, and the associating (i), (ii) employs the set of patient ID disambiguation rules operating on the timestamps of the one or more timestamped patient ID entries relative to the time gap and on strength measures of the one or more timestamped patient ID entries.

6. The apparatus as set forth in claim 1, wherein the patient ID resolution module is further configured to perform the associating operations (i), (ii) further based on information on proximity of the medical device to a patient corresponding to one of a group consisting of the first patient ID information and the second patient ID information when said patient data was generated.

7. The apparatus as set forth in claim 1, further comprising:

a patient records database configured to store the pre-gap patient data associated with the first patient ID information and the post-gap patient data associated with the second patient ID information;

wherein the patient ID resolution module is further configured to perform the associating operations (i), (ii) further based on information on whether the patient data having the time gap are duplicative of patient data already stored in the patient records database.

8. The apparatus as set forth in claim 7, wherein the patient ID resolution module is configured to perform the associating operations (i), (ii) based on information on whether the patient data having the time gap are duplicative of patient data already stored in the patient records database based on a continuity check comparing the patient data having the time gap with the duplicative patient data already stored in the patient records database.

9. An apparatus comprising:

a patient identification (ID) resolution module comprising a digital processor configured to disambiguate patient ID for patient data acquired over a time interval by a medical device, the patient data having a time gap and including pre-gap patient data preceding the time gap and post-gap patient data succeeding the time gap and further having one or more timestamped patient ID entries associated with the patient data, the patient ID resolution module (i) associating first patient ID information with the pre-gap patient data and (ii) associating second patient ID information with the post-gap patient data, the associating (i), (ii) being based on the one or more timestamped patient ID entries associated with the patient data and employing a set of patient ID disambiguation rules operating on the timestamps of the one or more timestamped patient ID entries relative to the time gap;

wherein the set of patient ID disambiguation rules further operate on strength measures of the one or more timestamped patient ID entries.

10. The apparatus as set forth in claim 9, wherein the strength measure of each timestamped patient ID entry is selected from a group consisting of a weak patient ID entry and a strong patient ID entry.

11. The apparatus as set forth in claim 9, wherein the strength measures of each timestamped patient ID entry is selected based on a patient ID entry modality used to enter the timestamped patient ID entry.

* * * * *